United States Patent [19]

Pfister

[11] 4,348,519
[45] Sep. 7, 1982

[54] THIAZINE DERIVATIVES

[75] Inventor: Rudolf Pfister, Basel, Switzerland

[73] Assignee: Hoffmann-La Roche Inc., Nutley, N.J.

[21] Appl. No.: 150,507

[22] Filed: May 16, 1980

[30] Foreign Application Priority Data

Jun. 13, 1979 [CH] Switzerland ............... 5528/79
Mar. 25, 1980 [CH] Switzerland ............... 2325/80

[51] Int. Cl.³ .................................. C07D 513/04
[52] U.S. Cl. .......................... 544/33; 424/246
[58] Field of Search ................ 424/246; 544/33

[56] References Cited

U.S. PATENT DOCUMENTS 4,076,709  2/1978  Hromatka et al. ............ 544/48
4,090,020  3/1978  Binder et al. ................. 544/48
4,187,303  2/1980  Hromatka et al. ............ 424/246
4,259,336  3/1981  Engel et al. .................. 544/33

FOREIGN PATENT DOCUMENTS 2704485  8/1978  Fed. Rep. of Germany.
2838377  3/1980  Fed. Rep. of Germany.

Primary Examiner—John M. Ford
Attorney, Agent, or Firm—Jon S. Saxe; Bernard S. Leon; William G. Isgro

[57] ABSTRACT

The invention relates to thiazine derivatives of the formula

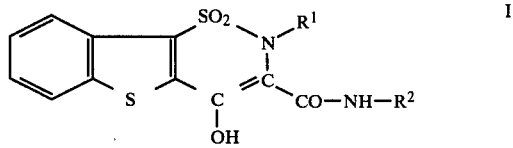

wherein $R^1$ is lower alkyl and $R^2$ is the residue of an aromatic heterocycle containing 1 to 4 hetero atoms optionally substituted by one or two lower alkyl groups, or a phenyl or benzyl group optionally substituted by halogen, hydroxy, lower alkyl, trifluoromethyl, nitro or lower alkoxy, and pharmaceutically acceptable salts thereof. The compounds of formula I are useful for the control or prevention of inflammation, pains, rheumatics and thromboses.

6 Claims, No Drawings

THIAZINE DERIVATIVES

BRIEF SUMMARY OF THE INVENTION

The invention relates to thiazine derivatives of the formula

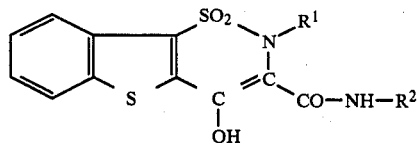

wherein $R^1$ is lower alkyl and $R^2$ is the residue of an aromatic heterocycle containing 1 to 4 hetero atoms which may be optionally substituted by one or two lower alkyl groups, or a phenyl or benzyl group which may be optionally substituted by halogen, hydroxy, lower alkyl, trifluoromethyl, nitro or lower alkoxy, or pharmaceutically acceptable salts thereof. The compounds of formula I are suitable for the control or prevention of inflammations, pains, rheumatics and thromboses.

In another aspect, the invention relates to intermediates of the formulas

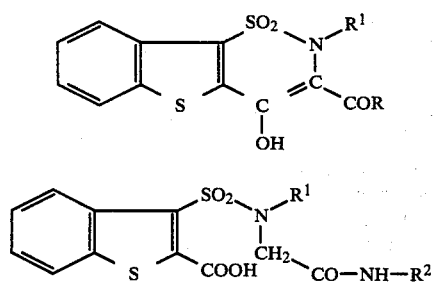
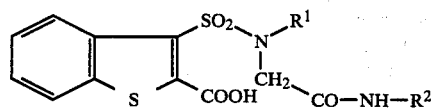
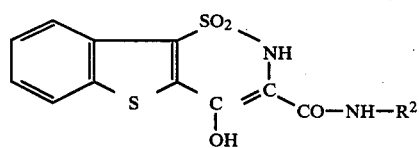
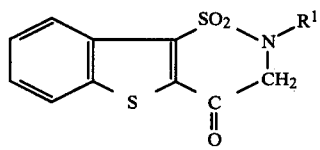
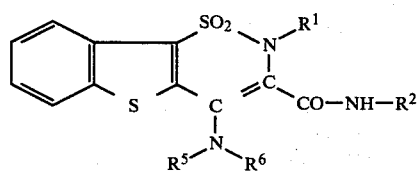

wherein $R, R^1, R^2, R^5$ and $R^6$ are as hereinafter described and reactive functional derivatives of compounds of formula IV.

DETAILED DESCRIPTION OF THE INVENTION

The invention relates to benzothienothiazine derivatives of the formula

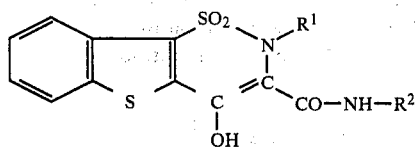

wherein $R^1$ is lower alkyl and $R^2$ is the residue of an aromatic heterocycle containing 1 to 4 hetero atoms optionally substituted by one or two lower alkyl groups, or $R^2$ is a phenyl or benzyl group optionally substituted by halogen, hydroxy, lower alkyl, trifluoromethyl, nitro or lower alkoxy.

The invention relates to compounds of formula I and pharmaceutically usable or acceptable salts thereof, and intermediates for the preparation of said compounds, medicament composition containing a compound of formula I or a pharmaceutically acceptable salt thereof, as well as the use of compounds of formula I or of pharmaceutically acceptable salts thereof in the control or prevention of illnesses.

As used herein, the term "lower alkyl" denotes a straight-chain or branched-chain saturated hydrocarbon group containing 1–4 carbon atoms, for example, methyl, ethyl, propyl, isopropyl, tert. butyl, and the like. The term "lower alkoxy" denotes alkyloxy groups containing up to 4 carbon atoms, for example, methoxy, ethoxy, propoxy, isopropoxy, tert. butoxy, and the like. The term "halogen" denotes chlorine, bromine, fluorine and iodine. The term "residue of an aromatic heterocycle containing 1 to 4 hetero atoms optionally substituted by one or two lower alkyl groups" includes residues of 5-membered and 6-membered aromatic heterocycles containing 1 to 4 nitrogen and/or oxygen and/or sulfur atoms, for example, 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl and the like.

The term "phenyl or benzyl group optionally substituted by halogen, hydroxy, lower alkyl, trifluoromethyl, nitro or lower alkoxy" includes, for example, phenyl, 4-hydroxyphenyl, 3-tolyl, 3-chlorophenyl, 4-fluorophenyl, 3-trifluoromethylphenyl, 2,4-dichlorophenyl, 4-bromophenyl, 4-chlorophenyl, 4-nitrophenyl, 2-tolyl, 2,5-dichlorophenyl, 4-nitro-2-tolyl, 4-iodophenyl, 4-n-butylphenyl, benzyl, 2-chlorophenyl and the like.

In a preferred group of compounds of formula I, $R^1$ is methyl. $R^2$ preferably is pyridyl optionally monosubstituted by lower alkyl; 2-pyridyl and 6-methyl-2-pyridyl are especially preferred. Phenyl is another representative group for $R^2$.

An especially preferred compound of formula I is 4-hydroxy-2-methyl-N-(2-pyridyl)-2H-[1]benzo-thieno[2,3-e]-1,2-thiazine-3-carboxamide 1,1-dioxide.

Other representative compounds of formula I are 4-hydroxy-2-methyl-N-(6-methyl-pyridyl-2)-2H-[1]benzothieno[2,3-e]-1,2-thiazine-3-carboxamide 1,1-dioxide and 4-hydroxy-2-methyl-N-phenyl-2H-[1]benzo-thieno[2,3-e]-1,2-thiazine-3-carboxamide 1,1-dioxide.

The benzothienothiazine derivatives of formula I and their pharmaceutically acceptable salts can be prepared in accordance with the invention by
(a) reacting a compound of the formula

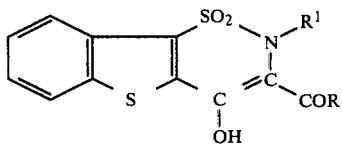

wherein R¹ is as previously described, and R is lower alkoxy or a group of the formula —NR³R⁴ wherein R³ and R⁴, independently, is hydrogen or lower alkyl, or together with the nitrogen atom is a heterocycle, with an amine of the formula

    III wherein R² is as previously described,
or
(b) cyclizing a reactive functional derivative of an acid of the formula

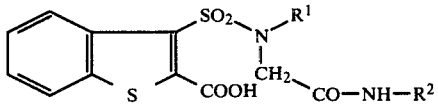

wherein R¹ and R² are as previously described, or
(c) appropriately alkylating a compound of the formula

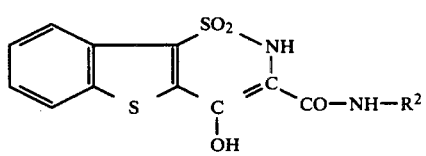

wherein R² is as previously described, or
(d) reacting a compound of the formula

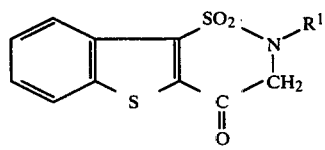

wherein R¹ is as previously described, in the presence of a strong base with an isocyanate of the formula

    VII wherein R² is as previously described, or
(e) hydrolyzing an enamine of the formula

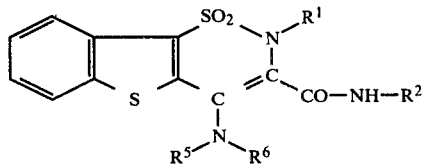

wherein R¹ and R² are as previously described, and R⁵ and R⁶ each is lower alkyl or together with the nitrogen atom is pyrrolin-1-yl, pyrrolidin-1-yl, piperidino, morpholino or 4-(lower alkyl)-piperazin-1-yl, or
(f) converting a compound of formula I into a pharmaceutically acceptable salt.

The reaction according to process embodiment (a) can be carried out in the presence or absence of an inert solvent. Suitable solvents are hydrocarbons such as benzene, toluene, xylene, and the like; halogenated hydrocarbons such as chloroform, chlorobenzene, methylene chloride, carbon tetrachloride, and the like; or dimethylformamide or dioxane. The reaction is preferably carried out while heating; the melting or reflux temperature of the reaction mixture is especially preferred. In certain cases, an excess of the amine of formula III may be utilized. When R in formula II is lower alkoxy, then the lower alkanol resulting in the reaction is preferably removed by distillation azeotropically from the reaction mixture. When R in formula II is a group of the formula —NR³R⁴, then R³ and R⁴ can both be hydrogen or one can be hydrogen and the other lower alkyl, for example, methyl, or both can be lower alkyl, for example, methyl; when R³ and R⁴ together with the nitrogen atom is a heterocycle, then this is primarily a 5-membered to 7-membered saturated heterocyclic group which, in addition to the mentioned nitrogen atom, can contain an oxygen atom such as pyrrolidin-1-yl, piperidino, morpholino and the like.

According to process embodiment (b), a reactive functional derivative of an acid of formula IV is cyclized. This cyclization is carried out in the presence of a base and preferably in the presence of a solvent at a temperature in the range of from about 0° C. to about the reflux temperature of the cyclization mixture, preferably in the range of from room temperature to 60° C. Especially suitable bases are hydrides, amides or alcoholates of alkali metals. Suitable solvents are aprotic and protic solvents such as alcohols, for example, methanol and ethanol, ethers, for example, dioxane and acid amides, for example, dimethylformamide. Conveniently, the cyclization is carried out by dissolving the starting material of formula IV in the solvent, treating the solution with the base and leaving the mixture to stand for 1 to 4 hours at room temperature or heating the mixture to a temperature up to 60° C. Especially suitable reactive functional derivatives of the acids of formula IV are the corresponding lower alkyl esters, for example, the methyl esters.

According to process embodiment (c), a compound of formula V is alkylated. The alkylation is conveniently carried out by dissolving the starting material of formula V in an aprotic solvent such as acetonitrile, dioxane or dimethylformamide, forming the alkali metal salt using an alkali metal amide or hydride and then converting the salt into the corresponding compound of formula I by treatment with an alkylating agent, preferably an alkyl halide or sulfate. The temperature and pressure are not critical for this embodiment of the process, but for the sake of simplicity the alkylation is preferably carried out at room temperature and atmospheric pressure.

According to process embodiment (d), a compound of formula VI is reacted in the presence of a strong base with an isocyanate of formula VII. Suitable strong bases are alkali amides, alkali metal hydrides, alkaline earth hydrides and alkali metals. The reaction is preferably carried out under an inert gas, for example, nitrogen, at a temperature in the range of from about 0° C. to about 50° C., preferably at room temperature, and in the presence of an inert solvent, for example, toluene, dioxane, dimethylformamide, dimethylsulfoxide or hexamethylphosphoric acid triamide (HMPT).

The isocyanate starting materials of formula VII are either known or can be prepared in an analogous manner to the known members.

According to process embodiment (e), an enamine of formula VIII is hydrolyzed. The hydrolysis is preferably carried out using an aqueous mineral acid such as hydrochloric acid, hydrobromic acid, hydroiodic acid or sulfuric acid or using trifluoroacetic acid, whereby it is carried out at a temperature in the range of from about 50° C. to about the boiling point of the mixture, preferably at the boiling point of the mixture. In this hydrolysis, the acid simultaneously serves as the solvent.

The starting materials of formula II used in process embodiment (a) can be prepared in a known manner starting from known compounds. In particular, they can be prepared in accordance with Reaction Scheme I hereinafter wherein $R^1$, $R^3$ and $R^4$ are as previously described and R' is lower alkyl and in accordance with the specific details given in Examples 1 and 7.

Reaction Scheme I

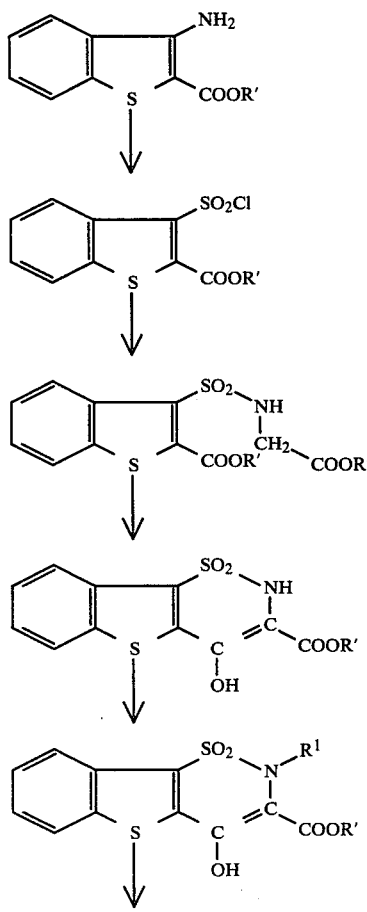

IX

X

XI

XII

IIa

-continued
Reaction Scheme I

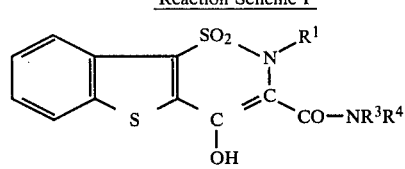

II b

Lower alkyl esters of acids of formula IV which can be used as the starting materials for process embodiment (b) can be prepared, for example, by reacting an amine of formula III with chloroacetyl chloride and reacting the resulting product of the formula $$Cl-CH_2-CO-NH-R^2 \qquad XIII$$

wherein $R^2$ is as previously described, with a compound of the formula

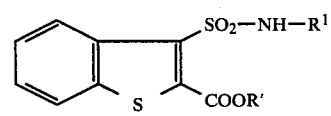

XIV wherein R', and $R^1$ are as previously described, or by reacting a compound of formula X with a compound of the formula $$R^1-NH-CH_2-CO-NH-R^2 \qquad XV$$

wherein $R^1$ and $R^2$ are as previously described. Other reactive functional derivatives of acids of formula IV can be prepared in a known manner from the esters obtained. Compounds of formula XIV can, in turn, be prepared, for example, by reacting a compound of formula X with an amine of the formula $$R^1-NH_2 \qquad XVI$$

wherein $R^1$ is as previously described.

Starting materials of formula V used in process embodiment (c) can be prepared, for example, by reacting a compound of formula XII with an amine of formula III. Conveniently, the nitrogen atom in the 2-position of the compound of formula XII can be protected, for example, with a suitable aralkyl group such as 4-methoxybenzyl, before the reaction with the amine of formula III, and after the reaction with the amine of formula III the protecting group can be cleaved.

Starting materials of formula VI used in process embodiment (d) can be prepared, for example, by hydrogenolyzing and decarboxylating a compound of formula IIa under acid conditions.

The preparation of the starting materials required for process embodiment (e) can be carried out according to Reaction Scheme II hereinafter, wherein $R^1$, $R^2$, $R^5$ and $R^6$ are as previously described and in accordance with the specific details given in Example 6.

Reaction Scheme II

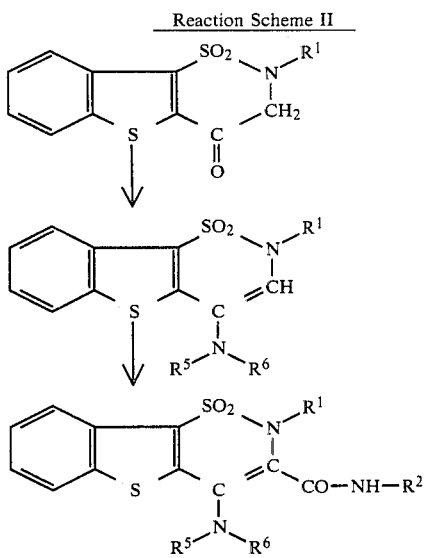

The compounds of formulas II, IV, V, VI and VIII also form part of the invention.

The compounds of formula I are acidic and can form pharmaceutically acceptable salts with pharmaceutically acceptable bases. Suitable pharmaceutically acceptable salts are, for example, alkali metal salts such as lithium, sodium and potassium salts; alkaline earth metal salts such as magnesium and calcium salts; and salts with amines such as triethanolamine, diethylaminoethanol, triethylamine, trimethylamine, diethylamine and the like. Compounds of formula I wherein $R^2$ is a basic heterocycle can also form pharmaceutically acceptable acid addition salts with pharmaceutically acceptable strong acids, such acids including, in particular, mineral acids, for example, hydrochloric acid.

The compounds of formula I and their salts possess an anti-inflammatory, analgesic and anti-rheumatic activity. These valuable pharmacological properties can be determined using standard methods; for example, the known kaolin-paw edema test on rats. In this test, an acute local inflammation is produced in the right hind paw of the rat by the intradermal injection of 0.1 ml. of a 10% kaolin suspension (bolus alba). The substance to be tested is administered orally and the following parameters are measured:

1. Diameter of the paw in mm (as an expression of the severity of the inflammation);
2. Pressure in grams on the paw to determine the pain threshold.

The substance to be tested is administered 0.5 hour before and 3.5 hours after the kaolin injection and the aforementioned parameters are measured 4 hours after the kaolin injection. The edema-inhibiting effect is given in percentages based on the difference in the edema intensity between untreated animals and animals treated with the substance to be tested, while the antinosiceptive activity is given by the percentage increase in the pain threshold.

In the foregoing test, 4-hydroxy-2-methyl-N-(2-pyridyl)-2H-[1]benzothieno[2,3-e]-1,2-thiazine-3-carboxamide 1,1-dioxide at a dosage of 1 mg/kg p.o. shows a 24% edema inhibition and a 66% increase in the pain threshold.

The compounds of formula I have an activity qualitatively similar to that of phenylbutazone which is known for its therapeutic use and properties. In addition, the compounds of formula I inhibit the blood platelet aggregation—as can be shown in a corresponding standard test—and accordingly also have antithrombotic properties.

The compounds of formula I and their pharmaceutically acceptable salts can be used as medicaments; for example, in the form of pharmaceutical preparations which contain them in association with a compatible pharmaceutical carrier material. This carrier material can be an organic or inorganic inert carrier material suitable for enteral or parenteral administration such as, for example, water, gelatin, gum arabic, lactose, starch, magnesium stearate, talc, vegetable oils, polyalkyleneglycols, petroleum jelly, and the like. The pharmaceutical preparations can be made up in a solid form, for example, as tablets, dragees, suppositories or capsules, in a semi-solid form, for example, as salves, or in a liquid form, for example, as solutions, suspensions or emulsions. If desired, the pharmaceutical preparations can be sterilized and/or can contain adjuvants such as preserving, stabilizing or emulsifying agents, salts for varying the osmotic pressure or buffers. They can also contain still other therapeutically valuable substances.

As mentioned earlier, compounds of formula I and their pharmaceutically acceptable salts can be used in the control or prevention of illnesses, especially in the control or prevention of inflammations, pains, rheumatics and thromboses. The dosage of a compound of formula I or its pharmaceutically acceptable salt which can be administered to a mammal can vary within fairly wide limits and is, of course, fitted to the individual requirements in each individual case. In general, an oral daily dosage of about 5 mg. to about 100 mg., preferably about 10 mg. to about 30 mg. can be utilized.

The invention also provides medicaments containing a compound of formula I or a pharmaceutically usable or acceptable salt thereof as well as a process for the preparation of such medicaments, which process comprises bringing one or more compounds of formula I or pharmaceutically acceptable salts thereof and, if desired, one or more additional therapeutically valuable substances into a galenical dosage form.

The Examples which follow further illustrate the invention. All temperatures are stated in degrees Centigrade, unless otherwise mentioned.

EXAMPLE 1

Preparation of the monosodium salt of 4-hydroxy-2-methyl-N-(2-pyridyl)-2H-[1]benzothieno[2,3-e]-1,2-thiazine-3-carboxamide 1,1-dioxide (a) 5 g. of 3-amino-2-carbomethoxy-benzothiophene, prepared according to J. Org. Chem. 37, 3224 (1972), are suspended at 0° C. in 40 ml. of concentrated hydrochloric acid. The mixture is diluted with 20 ml. of water and stirred at 0° C. for 10 minutes. A solution of 1.83 g. of sodium nitrate in 15 ml. of water is added dropwise at −15° C. and then the mixture is stirred at −15° C. for 40 minutes. A freshly prepared suspension obtained by combining a solution of 1.5 g. of cupric chloride in 3 ml. of water and 50 ml. of a 30% solution of sulfur dioxide in glacial acetic acid is rapidly added dropwise at −5° C. Then, the mixture is stirred without cooling for 4 hours and the suspension is poured into 400 ml. of water at 0° C. The resulting crystals are filtered off under suction, washed with water and dissolved in methylene chloride. The solution is dried over sodium sulfate and evaporated. The residue is recrystallized from methylene chloride with the addition of hexane. The 2-carbomethoxy-benzothiophene-3-sulfochloride obtained melts at 103°–105° C.

(b) 10.3 g. of the sulfochloride obtained in accordance with paragraph (a) and 4.45 g. of glycine ethyl ester hydrochloride are stirred at 23° C. overnight in 100 ml. of pyridine. The solvent is distilled off under reduced pressure and the residue is taken up in 500 ml. of methylene chloride. The mixture is washed at 0° C. with 2 N hydrochloric acid and water. The organic solution is dried over sodium sulfate and evaporated. The residue is recrystallized from methylene chloride with the addition of hexane. The N-(2-carbomethoxy-benzothiophene-3-sulfonyl)glycine methyl ester obtained melts at 148°–150° C.

(c) 1.55 g. of sodium are dissolved in 30 ml. of absolute methanol, the solution is evaporated at 11 Torr with the exclusion of moisture and the residue is dried at 0.11 Torr. The sodium methylate obtained is covered with 300 ml. of absolute toluene and 10 g. of the diester obtained in accordance with paragraph (b) are added. The mixture is stirred at 65° C. for 6 hours. After cooling, the dark red mixture is stirred into 800 ml. of water at 0° C. The aqueous phase is acidified with 2 N hydrochloric acid. The resulting crystals are filtered off under suction, washed with water and dried at 100° C./13 Torr. The 3-carbomethoxy-4-hydroxy-2H-[1]benzothieno[2,3-e]-1,2-thiazine 1,1-dioxide obtained melts at 240°–242° C.

(d) 1.69 g. of a 55% sodium hydride suspension in mineral oil are covered with 130 ml. of absolute dimethylformamide and treated with 5.5 g. of the benzothienothiazine obtained in accordance with paragraph (c). The mixture is stirred at 23° C. for 1 hour, then treated dropwise with 4.5 ml. of methyl iodide, stirred at 23° C. overnight and then evaporated at about 1 Torr. The residue is dissolved in 400 ml. of water at 0° C. By acidification with 2 N hydrochloric acid there are obtained crystals which are filtered off under suction and, after washing with water, dried at 100° C./0.01 Torr. The 3-carbomethoxy-4-hydroxy-2-methyl-2H-[1]benzothieno[2,3-e]-1,2-thiazine, 1,1-dioxide obtained melts at 183°–185° C.

(e) 5 g. of 3-carbomethoxy-4-hydroxy-2-methyl-2H-[1]benzothieno[2,3-e]-1,2-thiazine 1,1-dioxide and 3 g. of 2-aminopyridine are treated with 150 ml. of a xylene isomer mixture and heated so that the resulting methanol distils off azeotropically. After 6 hours, the mixture is left to cool to room temperature. The cyrstals obtained are filtered off under suction and washed with a xylene mixture. After recrystallization from dimethylformamide and addition of methanol, there is obtained 4-hydroxy-2-methyl-N-(2-pyridyl)-2H-[1]benzothieno[2,3-e]-1,2-thiazine-3-carboxamide 1,1-dioxide in the form of yellow crystals of melting point 222°–224° C.

(f) 774 mg. of 4-hydroxy-2-methyl-N-(2-pyridyl)-2H-[1]benzothieno[2,3-e]-1,2-thiazine-3-carboxamide 1,1-dioxide are suspended in 10 ml. of methanol and 20 ml. of 0.1 N sodium hydroxide are added. After stirring at room temperature for about 20 minutes, there results a clear solution which is evaporated at 11 Torr. The residue is dissolved in a small amount of methanol. By adding absolute diethyl ether there is obtained the monosodium salt of 4-hydroxy-2-methyl-N-(2-pyridyl)-2H-[1]benzothieno[2,3-e]-1,2-thiazine-3-carboxamide 1,1-dioxide in crystalline form having 0.69% water of crystallization and a melting point of 206°–208° C.

EXAMPLE 2

Preparation of 4-hydroxy-2-methyl-N-(6-methyl-pyridyl-2)-2H-[1]-benzothieno[2,3-e]1,2-thiazine-3-carboxamide 1,1-dioxide In a manner analogous to that described in paragraph (e) of Example 1, from 1.63 g. of 3-carbomethoxy-4-hydroxy-2-methyl-2H-[1]benzothieno[2,3-e]-1,2-thiazine 1,1-dioxide and 1.22 g. of 6-amino-2-methyl-pyridine in 50 ml. of o-xylene there is obtained 4-hydroxy-2-methyl-N-(6-methyl-pyridyl-2)-2H-[1]benzothieno[2,3-e]-1,2-thiazine-3-carboxamide 1,1-dioxide having a melting point of 250°–251° C.

EXAMPLE 3

Preparation of 4-hydroxy-2-methyl-N-phenyl-2H-[1]benzothieno[2,3-e]-1,2-thiazine-3-carboxamide 1,1-dioxide (a) 12.2 g. of 2-carbomethoxy-benzothiophene-3-sulfochloride are introduced at room temperature while stirring into 200 ml. of pyridine and 10 g. of sarcosine anilide hydrochloride are added thereto. The mixture is stirred overnight (16 hours) and then evaporated at 11 Torr. The residue is covered with methylene chloride and the mixture is shaken out at 0° C. with 2 N hydrochloric acid. The organic phase is washed with water, dried over sodium sulfate and evaporated at 11 Torr. The residue crystallizes from methylene chloride by the addition of petroleum ether. The 3-[N-(phenylcarbamoylmethyl)-N-methyl]-sulfamoyl-benzothieno-2-carboxylic acid methyl ester melts at 114°–117° C.

(b) 1.05 g. of the compound obtained according to paragraph (a) are dissolved in 50 ml. of absolute pyridine with the exclusion of moisture and 0.45 g. of pure sodium methylate is added. The mixture is stirred at 50° C. for 2 hours and then evaporated at 11 Torr. The residue is taken up in 100 ml. of water and extracted three times with 40 ml. of methylene chloride each time. The methylene chloride extracts are washed with 50 ml. of water. The aqueous solutions are combined, diluted with methanol, decolorized with charcoal, acidified to pH 2 with 2 N hydrochloric acid and the methanol is removed at 11 Torr. The precipitate is stirred with water and then dissolved in methylene chloride. The solution is stirred with 2 g. of silica gel and filtered. The filtrate is evaporated and the residue is stirred with diethyl ether. After filtration and drying at 11 Torr, there is obtained 4-hydroxy-2-methyl-N-phenyl-2H-[1]benzothieno[2,3-e]-1,2-thiazine-3-carboxamide 1,1-dioxide having a melting point of 261°–263° C.

EXAMPLE 4

Preparation of 4-hydroxy-2-methyl-N-(2-pyridyl)-2H-[1]benzothieno[2,3-e]-1,2-thiazine-3-carboxamide 1,1-dioxide (a) 935 mg. of 3-carbomethoxy-4-hydroxy-2H-[1]benzothieno[2,3-e]-1,2-thiazine 1,1-dioxide are dissolved in 10 ml. of absolute dimethylformamide and 290 mg. of a 55% sodium hydride dispersion in paraffin are added. The suspension is stirred at room temperature for 1 hour. Then, a solution of 730 mg. of 4-methoxybenzyl bromide in 5 ml. of absolute dimethylformamide is added dropwise within 30 minutes, the mixture is stirred at room temperature for a further 3 hours and then poured into 100 ml. of ice-cold water while stirring. The mixture is then acidified to pH 2 with concentrated hydrochloric acid. The precipitate which results is filtered off under suction and dissolved in methylene chloride. The solution is dried over sodium sulfate, filtered and evaporated. The residue crystallizes from methylene chloride after the addition of petroleum ether. The 3-carbomethoxy-4-hydroxy-2-(4-methoxybenzyl)-2H-[1]benzothieno[2,3-e]-1,2-thiazine 1,1-dioxide obtained melts at 163°–164° C.

(b) 1 g. of the compound obtained according to paragraph (a) and 550 mg. of 2-aminopyridine are dissolved in 30 ml. of o-xylene. The mixture is heated at 150° C. (bath temperature) for 6 hours while stirring, the resulting methanol being distilled off azeotropically. The mixture is then evaporated at 11 Torr. The residue is boiled with a mixture of 15 ml. of methylene chloride and 15 ml. of ether. The mixture is left to cool, the resulting precipitate is filtered off under suction and recrystallized from methylene chloride with the addition of petroleum ether. The 4-hydroxy-2-(4-methoxybenzyl)-N-(2-pyridyl)-2H-[1]benzothieno[2,3-e]-1,2-thiazine-3-carboxamide 1,1-dioxide obtained melts at 188°–190° C.

(c) 400 mg. of the compound obtained according to paragraph (b) are dissolved in 5 ml. of trifluoroacetic acid and 0.9 ml. of anisole are added. The mixture is stirred at 50° C. for 16 hours and then evaporated at 11 Torr. The residue is stirred with ether and filtered. The filter cake is dissolved in dilute sodium hydroxide, the solution is decolorized with charcoal, filtered and the filtrate is neutralized with 2 N hydrochloric acid. The crystals are filtered off under suction, washed with water and dried for 4 hours at 100° C./13 Torr. The 4-hydroxy-N-(2-pyridyl)-2H-[1]benzothieno[2,3-e]-1,2-thiazine-3-carboxamide 1,1-dioxide obtained melts at 240°–242° C.

(d) 790 mg. of the compound obtained according to paragraph (c) are dissolved in 10 ml. of absolute dimethylformamide and 93 mg. of a 55% sodium hydride dispersion in paraffin are added. The mixture is stirred at room temperature for 45 minutes, 2 ml. of methyl iodide are added dropwise at 0° C. and the mixture is stirred at room temperature for 4 hours. The mixture is stirred into ice/water and neutralized with 2 N hydrochloric acid. The precipitate is filtered off under suction and dissolved in chloroform with the addition of methanol. The solution is dried over sodium sulfate and filtered over 20 g. of silica gel. The eluate is evaporated at 11 Torr. and the residue is stirred with acetonitrile. After filtering off under suction and drying, the resulting crystals of 4-hydroxy-2-methyl-N-(2-pyridyl)-2H-[1]benzothieno[2,3-e]-1,2-thiazine-3-carboxamide 1,1-dioxide melt at 222°–224° C.

EXAMPLE 5

Preparation of 4-hydroxy-2-methyl-N-phenyl-2H-[1]benzothieno[2,3-e]-1,2-thiazine-3-carboxamide 1,1-dioxide (a) 10 g. of 3-carbomethoxy-4-hydroxy-2-methyl-2H-[1]benzothieno[2,3-e]-1,2-thiazine 1,1-dioxide are added to a mixture of 200 ml. of glacial acetic acid and 200 ml. of concentrated hydrochloric acid. The mixture is then boiled under reflux at an oil-bath temperature of 140° C. for 18 hours. The content of the flask is evaporated at 11 Torr. and the residue is suspended in 300 ml. of water. The crystals obtained are filtered off under suction and dissolved in 300 ml. of methylene chloride. The solution is dried over sodium sulfate, filtered over 50 g. of silica gel and treated with petroleum ether, whereafter 3,4-dihydro-2-methyl-4-oxo-2H-[1]benzothieno[2,3-e]-1,2-thiazine 1,1-dioxide crystallizes out. After drying over phosphorus pentoxide at 50° C./0.01 Torr for 12 hours, this compound melts at 184°–186° C.

(b) 2.67 g. of 3,4-dihydro-2-methyl-4-oxo-2H-[1]benzothieno[2,3-e]-1,2-thiazine 1,1-dioxide are dissolved in 40 ml. of absolute dimethylformamide and 1.2 ml. of phenylisocyanate are added. The solution obtained is added dropwise at 4° C. within 30 minutes to a suspension of 600 mg. of a 55% sodium hydride dispersion in paraffin in 10 ml. of dimethylformamide. The mixture is stirred for a further 1 hour at 4° C. and subsequently for 2 hours at 27° C. and then stirred into 400 ml. of ice/water. The solution obtained is acidified with concentrated hydrochloric acid. The precipitate is filtered off under suction, washed with water and dissolved in methylene chloride. The resulting solution is dried over sodium sulfate and evaporated. The residue is stirred with 30 ml. of methanol. The insoluble components are digested with acetonitrile, filtered off under suction and dried for 4 hours at 100° C./11 Torr. The 4-hydroxy-2-methyl-N-phenyl-2H-[1]benzothieno[2,3-e]-1,2-thiazine-3-carboxamide 1,1-dioxide obtained melts at 261°–263° C.

EXAMPLE 6

Preparation of 4-hydroxy-2-methyl-N-(2-pyridyl)-2H-[1]benzothieno[2,3-e]-1,2-thiazine-3-carboxamide 1,1-dioxide (a) 1.4 g. of 3,4-dihydro-2-methyl-4-oxo-2H-[1]benzothieno[2,3-e]-1,2-thiazine 1,1dioxide, 0.9 ml. of pyrrolidine and 10 mg. of p-toluenesulfonic acid monohydrate are boiled in 20 ml. of benzene for 6 hours on a water separator. The solution is evaporated at 11 Torr, the residue is dissolved in methylene chloride and the solution is filtered over silica gel. By the addition of petroleum ether there crystallizes out 2-methyl-4-(1-pyrrolidinyl)-2H-[1]benzothieno[2,3-e]-1,2-thiazine 1,1-dioxide having a melting point of 164°–166° C.

(b) 2.1 g of the compound obtained according to paragraph (a) and 1.3 ml. of triethylamine are dissolved in 50 ml. of absolute tetrahydrofuran. 4 ml. of a 20% solution of phosgene in toluene are added dropwise at 0°–5° C. and the mixture is warmed at 50° C. for 3 hours. After adding 1.3 ml. of triethylamine and 880 mg. of 2-aminopyridine, the mixture is stirred at 50° C. for a further 2 hours. After cooling, the mixture is stirred into 180 ml. of water and the resulting mixture is extracted with methylene chloride. An insoluble precipitate is filtered off (melting point 325° C.). The methylene chloride solution is dried over sodium sulfate and chromatographed over 100 g. of silica gel. The 2-methyl-N-(2-pyridyl)-4-(1-pyrrolidinyl)-2H-[1]benzothieno[2,3-e]-1,2-thiazine-3-carboxamide 1,1-dioxide melts at 183°–185° C.

(c) The compound obtained according to paragraph (b) is dissolved in 2 ml. of 2 N hydrochloric acid and heated at 100° C. for 10 minutes. The solution is neutralized with 2 N sodium carbonate solution and extracted with methylene chloride. The organic phase is dried over sodium sulfate and evaporated. The 4-hydroxy-2-methyl-N-(2-pyridyl)-2H-[1]benzothieno[2,3-e]-1,2-thiazine-3-carboxamide 1,1-dioxide is obtained by stirring with ether and melts at 222° C.

EXAMPLE 7

Preparation of 4-hydroxy-2-methyl-N-(2-pyridyl)-2H-[1]benzothieno[2,3-e]-1,2-thiazine-3-carboxamide 1,1-dioxide (a) 2 g. of 3-carbomethoxy-4-hydroxy-2-methyl-2H-[1]benzothieno[2,3-e]-1,2-thiazine 1,1-dioxide are dissolved in 100 ml. of o-xylene and stirred at 150° C. Ammonia is conducted in for 8 hours, the mixture is cooled and then filtered under suction. The residue is stirred with methylene chloride, filtered off under suction and dried at 11 Torr. The 4-hydroxy-2-methyl-2H-[1]benzothieno[2,3-e]-1,2-thiazine-3-carboxamide 1,1-dioxide melts at 247°–248° C. (with decomposition).

(b) 1.5 g. of the compound obtained according to paragraph (a) and 850 mg. of 2-aminopyridine are boiled under reflux (bath temperature 150° C.) in 100 ml. of o-xylene for 20 hours. The mixture is evaporated, the residue is dissolved in chloroform and the solution is filtered over silica gel. The 4-hydroxy-2-methyl-N-(2-pyridyl)-2H-[1]benzothieno[2,3-e]-1,2-thiazine-3-carboxamide 1,1-dioxide melts, after trituration with acetone and drying, at 224°–225.5° C.

EXAMPLE A

Suppositories of the following composition are prepared in the usual manner:

|  | Per Suppository |
|---|---|
| 4-Hydroxy-2-methyl-N-(2-pyridyl)-2H-[1]-benzothieno[2,3-e]-1,2-thiazine-3-carboxamide 1,1-dioxide | 0.020 g. |
| Hydrogenated coconut oil | 1.235 g. |
| Carnauba wax | 0.045 g. |

EXAMPLE B

Tablets of the following composition are prepared in the usual manner:

|  | Per Tablet |
|---|---|
| 4-Hydroxy-2-methyl-N-(2-pyridyl)-2H-[1]benzothieno[2,3-e]-1,2-thiazine-3-carboxamide 1,1-dioxide | 10.0 mg. |
| Lactose | 80.0 mg. |
| Maize starch | 9.0 mg. |
| Magnesium stearate | 1.5 mg. |

EXAMPLE C

Capsules containing the following ingredients are prepared in the usual manner:

|  | Per Capsule |
|---|---|
| 4-Hydroxy-2-methyl-N-(2-pyridyl)-2H-[1]-benzothieno[2,3-e]-1,2-thiazine-3-carboxamide 1,1-dioxide | 10.0 mg. |
| Lactose | 165.0 mg. |
| Maize starch | 30.0 mg. |
| Talc | 5.0 mg. |

I claim:

1. A compound of the formula

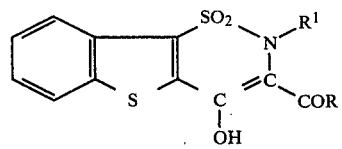

II wherein $R^1$ is lower alkyl and R is a group of the formula $-NR^3R^4$ wherein $R^3$ and $R^4$ each is hydrogen or lower alkyl or together with the nitrogen atom is a 5-membered to 7-membered saturated heterocyclic group which can contain an oxygen atom.

2. The compound in accordance with claim 1, 4-hydroxy-2-methyl-2H-[1]-benzothieno[2,3-e]-1,2-thiazine-3-carboxamide 1,1-dioxide.

3. A compound of the formula

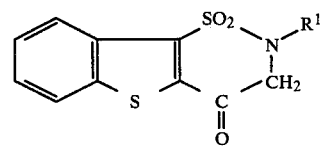

VI wherein $R^1$ is lower alkyl.

4. The compound in accordance with claim 3, 3,4-dihydro-2-methyl-4-oxo-2H-[1]benzothieno[2,3-e]-1,2-thiazine 1,1-dioxide.

5. A compound of the formula

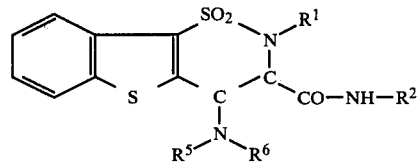

VIII wherein $R^1$ is lower alkyl and $R^2$ is 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl; phenyl; phenyl substituted by halogen, hydroxy, lower alkyl, trifluoromethyl, nitro or lower alkoxy; benzyl; or benzyl substituted by halogen, hydroxy, lower alkyl, trifluoromethyl, nitro or lower alkoxy; $R^5$ and $R^6$ each is lower alkyl or together with the nitrogen atom is pyrrolin-1-yl, pyrrolidin-1-yl, piperidino, morpholino or 4-(lower alkyl)-piperazin-1-yl.

6. The compound in accordance with claim 5, 2-methyl-N-(2-pyridyl)-4-(1-pyrrolidinyl)-2H-[1]benzothieno[2,3-e]-1,2-thiazine-3-carboxamide 1,1-dioxide.

* * * * *